ent to the Patent Office.

United States Patent [19]
Seko et al.

[11] 4,159,284
[45] Jun. 26, 1979

[54] PROCESS FOR SEPARATION OF HYDROCARBON MIXTURE

[75] Inventors: Maomi Seko; Tetsuya Miyake, both of Tokyo; Kunihiko Takeda; Tatsushi Saeki, both of Yokohama, all of Japan

[73] Assignee: Asahi Kasei Kogyo Kabushiki Kaisha, Osaka, Japan

[21] Appl. No.: 869,634

[22] Filed: Jan. 12, 1978

Related U.S. Application Data

[63] Continuation of Ser. No. 621,504, Oct. 10, 1975, abandoned.

[30] Foreign Application Priority Data

| Oct. 16, 1974 | [JP] | Japan | 49-118963 |
| Oct. 16, 1974 | [JP] | Japan | 49-118964 |
| Dec. 14, 1974 | [JP] | Japan | 49-143919 |
| Dec. 14, 1974 | [JP] | Japan | 49-143920 |
| Dec. 16, 1974 | [JP] | Japan | 49-144333 |
| Mar. 8, 1975 | [JP] | Japan | 50-28374 |
| Mar. 28, 1975 | [JP] | Japan | 50-36823 |
| Apr. 7, 1975 | [JP] | Japan | 50-41994 |

[51] Int. Cl.$^2$ .................... C07C 7/12; C07C 7/13
[52] U.S. Cl. .................... 585/478; 208/310 R; 208/310 Z; 585/821; 585/825
[58] Field of Search .................. 260/666 SA, 676 AD, 260/674 SA, 674 A; 208/310 R, 310 Z

[56] References Cited

U.S. PATENT DOCUMENTS

| 2,776,250 | 1/1957 | Capell et al. | 260/674 SA |
| 3,176,444 | 4/1965 | Kiyonga | 208/310 R |
| 3,761,533 | 9/1973 | Otani et al. | 260/674 SA |
| 3,894,108 | 7/1975 | Geissler | 260/674 SA |
| 3,939,221 | 2/1976 | Pearce | 260/674 SA |

*Primary Examiner*—Delbert E. Gantz
*Assistant Examiner*—C. E. Spresser
*Attorney, Agent, or Firm*—Cooper, Dunham, Clark, Griffin & Moran

[57] ABSTRACT

A hydrocarbon mixture is fed to a system of adsorbents in a plug flow so as to form at least one displacement boundary in the system to accumulate the composition in the vicinity of the boundary. The process is simple to operate and suitable for separation of a hydrocarbon mixture containing components with similar physical and chemical properties such as a mixture of hydrocarbon isomers.

6 Claims, 12 Drawing Figures

PROCESS FOR SEPARATION OF HYDROCARBON MIXTURE

This is a continuation of application Ser. No. 621,504 filed Oct. 10, 1975 now abandoned.

This invention relates to a process for separating hydrocarbons by using adsorbents having selective adsorption ability.

A typical process of prior art for separation of a hydrocarbon mixture by selective adsorption methods comprises adsorbing substances to be separated onto adsorbents, followed by removal of residual unadsorbed mixture, and then recovering the adsorbed substance (hereinafter referred to as "batch process"). Said process is known to be advantageous when there is a great difference in the relative adsorptions between components or when the desired composition is near the composition of the starting mixture. Accordingly, the batch process is utilized for industrial applications only when separation can be achieved with relative ease. The aforesaid procedure can be repeated for several times until the desired composition is obtained in case a single step operation does not yield the desired product. Therefore, in those cases where the difference in relative adsorption is small, or the desired composition differs considerably from that of the starting material, it is required in batch process to repeat many cycles of operation.

More recently, continuous processes have been proposed for selective adsorption to separate relatively large quantities of difficulty separable substances, which are industrially practiced especially for separation of aromatic hydrocarbons having very similar volatilities and chemical properties, as disclosed by U.S. Pat. Nos. 3,558,732, 3,686,342 and 3,707,550. These processes are characterized as "elution liquid chromatography" from the viewpoint of analytical chemistry. The details of elution liquid chromatography are discussed in detail by D. B. Broughton in "Continuous Adsorptive Processing—A New Separation Technique" 34th Annual Meeting, The Society of Chemical Engineers, Tokyo, Japan, Apr. 2, 1969. In this process, a suitable quantity of the feed mixture to be separated is adsorbed onto adsorbents having selective adsorption power which are packed within a development column. Then, a developing liquid (i.e. "carrier" according to the terminology of analytical chemistry), which is a substance having an adsorption ability substantially equal to or slightly lower than those of the principal components in the feed mixture is supplied onto the column to develop the mixture over the adsorbents. A large quantity of the developing liquid thereby flows in a stream to move the adsorbed mixture on the adsorbents at different speed for each individual component in the mixture.

Thus separation is achieved between substances which move relatively slowly and those which move at a relatively higher rate. From the standpoint of industrial applications, however, this process involves the following drawbacks partly because the development is carried out by using a large quantity of developing agent.

1. The concentrations of the substances to be separated in the column progressively decreased, so that only a portion of adsorption capacity of the adsorbents can be effectively utilized.
2. The separated substances are accompanied by a large quantity of developing agent when recovered from the column;
3. Generally speaking, the higher the ratio of developing agent to feed mixture, the better the separation efficiency, so that development at high concentration would decrease efficiency;
4. The fractions of the substances in the development column are distributed in the form of a Gaussian distribution curve when the operation is conducted ideally, and therefore the so called tail fractions of the Gaussian distribution must be recovered for collecting a highly purified substance, where only very diluted substances with developing agent can be obtained.

These drawbacks are due to the basic principles of the elution liquid chromatography. That is, the separation in elution chromatography is achieved when a large quantity of developing agent, whose relative adsorption ability is equal to or a little lower than those of substances to be separated, passes the adsorption band of the feed substances. In other words, it is essential to choose a developing agent which can pass the adsorption band of the feed substances, so that the Gaussian distribution of each component in the feed mixture is developed in the adsorbents' bed.

As described above, the batch separation processes, although the operation steps are simple, can only be effective when the relative adsorption ability of the feed components differs substantially from each other, while the complicated separation processes by elution liquid chromatography may yield very pure, but diluted product with developing agent.

The object of the present invention is to provide a continuous process for separation of a hydrocarbon mixture by adsorbing feed mixture on adsorbents with operation steps which are as simple as the batch separation process, even when the relative adsorption power between feed components does not differ greatly. More specifically, the present invention provides a process for separation of a hydrocarbon mixture by using a system of adsorbents which selectively adsorb the components of the mixture, and the adsorbed hydrocarbons move along the packed adsorbents while forming clear displacement boundaries in which certain components are concentrated in the boundary region.

Thus, in its broadest sense, the present invention can be defined as a process for separating a hydrocarbon mixture which comprises feeding a hydrocarbon mixture to a system of adsorbents in a plug flow, thereby forming at least one displacement boundary in the system to accumulate desired composition in the vicinity of the boundary, and recovering the thus accumulated compositions.

The invention will be better understood by reference to the accompanying drawings, in which:

FIG. 1 (a) shows the embodiment wherein no substance other than the feed mixture is used; FIG. 1 (b) the embodiment wherein both front and rear displacement substances are used; and FIG. 1 (c) the embodiment wherein the mixture and a displacement substance are fed alternately to the adsorbent system;

Figure 7:
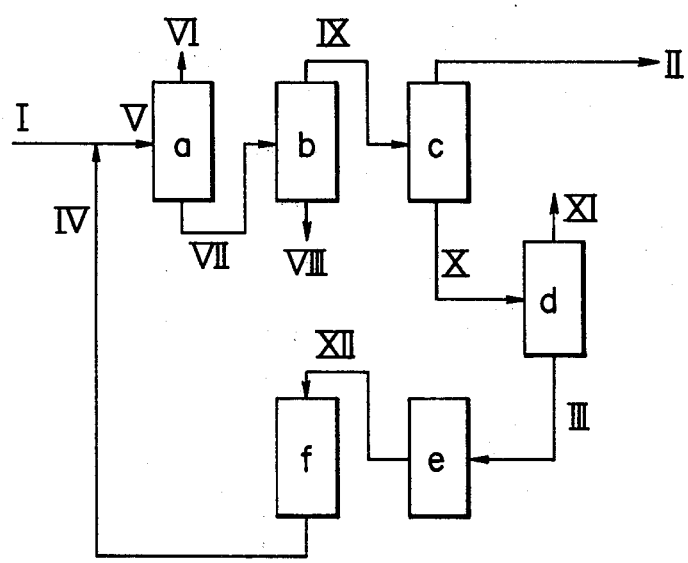
Figure 8:
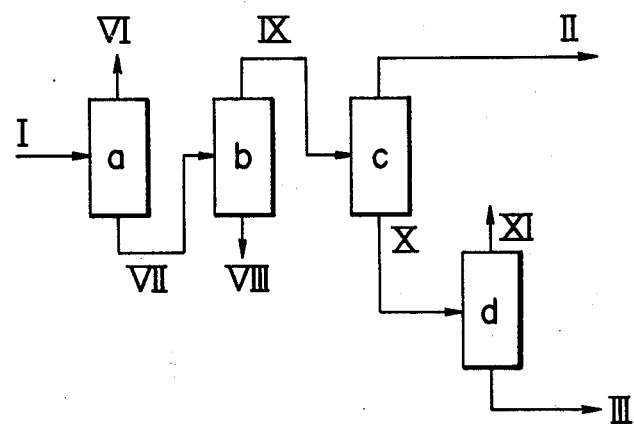

FIG. 7 shows flow diagram of another conbination of the separation process according to this invention with distillation and conversion units, which includes a light-cut distillation column a, a heavy-cut distillation column b, the main separation unit c, a distillation column d for recovering displacement substances, a preheater e and a conversion unit f, the numbers I to XII showing various directions to flow in the diagram;

FIG. 8 shows flow diagram of another example of combining distillation with the separation process of this invention, which includes a light-cut distillation column a, a heavy-cut distillation column b, the main separation unit c, and a distillation column d for recovering displacement substances.

Figure 9:
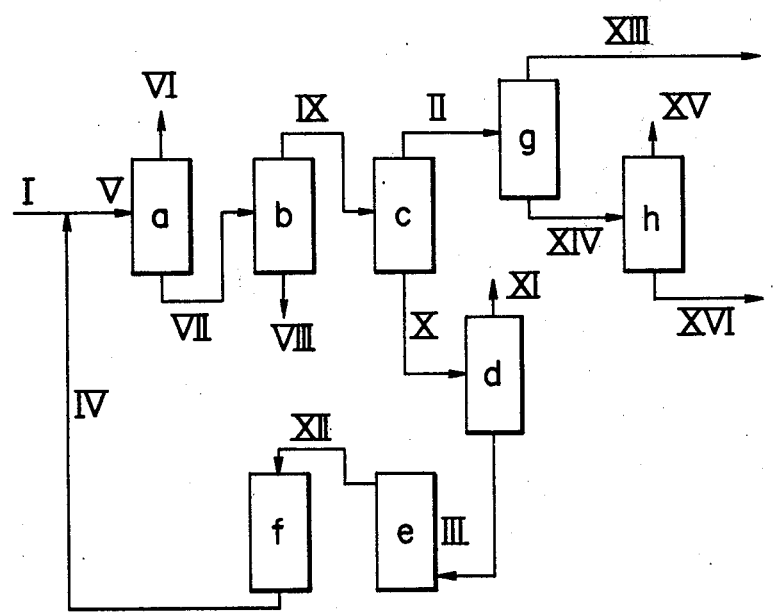

FIG. 9 shows flow diagram of a combined separation process for recovering two components from the feed mixture, which includes a light-cut distillation column a, a heavy-cut distillation column b, the main separation unit c, distillation columns d and h for recovering displacement substances, a preheater e and the conversion unit f, the numbers I to XVI designating various flow directions to in the diagram.

Figure 1C:
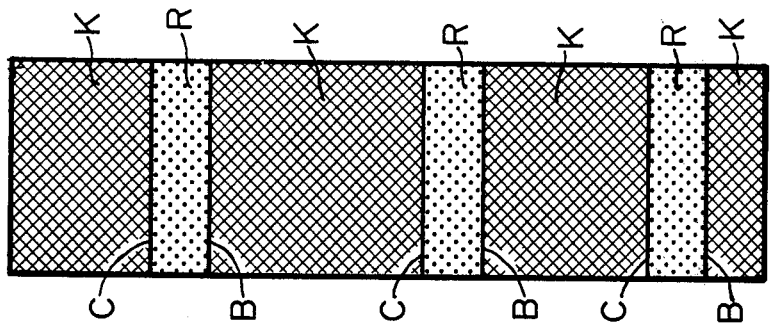
FIG. 1 shows flow diagrams of typical embodiments of the process to assist in explanation of general principles of this invention, where.
Figure 1B:
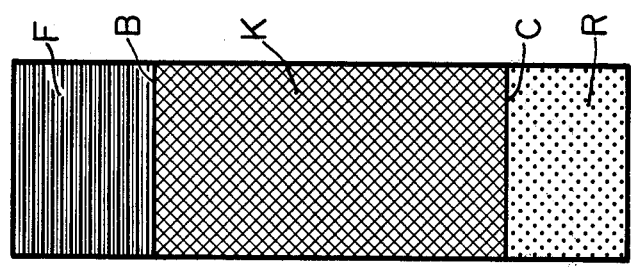
Figure 1A:
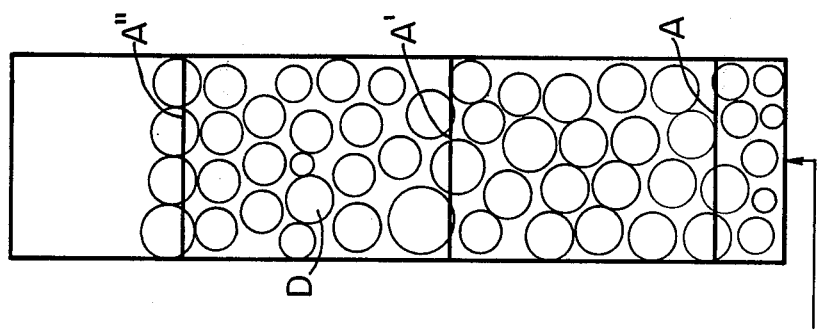

Referring now to FIG. 1 which is shown for explanation of the principles of separation in this invention, FIG. 1 (a) shows the most basic embodiment of this invention, wherein the feed hydrocarbon mixture is supplied to the bottom of the column packed with a selectively adsorbing material D. A part of the feed hydrocarbon mixture is adsorbed onto the adsorbent D while the rest of the mixture fills the interstices among the adsorbent particles. The feed mixture is introduced to the column as a plug flow so as to form a clear horizontal boundary A which moves towards a boundary A' while keeping its horizontal interface, when the feed mixture is continuously supplied to the column. During these steps of operation, liquid fraction in the neighborhood of the moving boundary A is enriched with components for which the adsorbent D has relatively weaker adsorption power and is depleted with those for which the adsorbent D has relatively stronger adsorption power.

By continuing this procedure, the said liquid fraction may reach a desired composition enriched with certain components in the feed mixture at the time of passing the boundary A, then the liquid may be recovered from the column as an effluent.

FIG. 1 (b) is another example of the separation process in which both front and rear displacement substances are used to enclose the feed hydrocarbon mixture in the column to form front, and rear boundaries recovering two different effluents from the vicinity of two boundaries respectively.

The adsorption band of the feed hydrocarbon mixture K is bounded in both sides with the adsorption band of front substance F and with that of rear substance R, to form boundaries of B between F and K, and C between K and R. In this case, relatively weakly-adsorbed components are similarly enriched in the neighbourhood of boundary B, whereas relatively strongly-adsorbed components are enriched around the boundary C, as shown in FIG. 1 (a), while these boundaries move along the adsorbent bed in the column. Thus, the components in the feed hydrocarbon mixture are arrayed in the adsorption band between boundaries B and C from the weakly-adsorbed ones to the strongly-adsorbed ones, the distribution of which gradually shifts to a higher degree of separation while the whole adsorption band physically moves forward in the developing column. As is clear from the above explanations, the desired components may be recovered from the effluent fractions in the neighbourhood of both boundaries.

FIG. 1 (c) is another embodiment of the present invention, wherein the same substance is used as the front and rear substances F and R, in FIG. 1 (b). Because the substance R in FIG. 1 (c) acts as both front and rear substances, the operation procedure can largely be simplified by feeding the column with the hydrocarbon mixture and the substance R.

Thus, specific embodiments herein contemplated, inclusive of those as described above are follows:

A. Only a hydrocarbon mixture is fed to the system of adsorbents in a plug flow, thereby forming only one front boundary in the system.

B. A front substance is filled in the system of adsorbents prior to feeding of the hydrocarbon mixture, thereby forming one front boundary in the system between said front substance and the hydrocarbon mixture.

C. A hydrocarbon mixture is first fed to the system of adsorbents to fill said system, followed by charging of a rear substance to the system in a plug flow, thereby forming one rear boundary in the system between the hydrocarbon mixture and the rear substance.

D. A front substance is filled in the system of adsorbents prior to feeding of the hydrocarbon mixture and a rear substance is charged in a plug flow after feeding the hydrocarbon mixture, thereby enclosing the feed hydrocarbon mixture in the system between the front and rear substances to form both front and rear boundaries, and recovering two different compositions from the vicinity of each of the two boundaries.

E. A substance of the same kind as the rear substance is filled in the system of adsorbents followed by feeding of the hydrocarbon mixture and thereafter a rear substance is charged in a plug flow to the system, thereby enclosing the feed hydrocarbon mixture between the substances of the same kind to form front and rear boundaries, and recovering two different compositions from the vicinity of each of the two boundaries, while maintaining the front boundary under conditions such that the front substance may not be penetrated into the adsorption band of the hydrocarbon mixture.

F. A substance of the same kind as the rear substance is filled in the system of adsorbents, followed by partial removal of said substance present in the interstices among the adsorbents out of the system prior to feeding of the hydrocarbon mixture, and a rear substance is charged in a plug flow to the system after feeding of the hydrocarbon mixture, thereby enclosing the feed hydrocarbon mixture in the system between the partly removed substance and the rear substance to form both front and rear boundaries, and recovering two different compositions from the vicinity of each of the two boundaries.

G. A single substance and a hydrocarbon mixture are fed in a plug flow to the system of adsorbents alternately, thereby enclosing the feed hydrocarbon mixture in the system between each pair of the substance to form front and rear boundaries, successively, and recovering successively two different compositions from the vicinity of each of the front and rear boundaries.

Furthermore, in practical applications, the following continuous processes are highly recommended:

H. By use of plural systems of adsorbents which are connected in series, a hydrocarbon mixture is separated in the first system in the manner according to any of the above embodiments to recover desired compositions, then the residual separated hydrocarbon mixture with or without supplemental feed of new hydrocarbon mixture into the next system is transferred into the next system to continue further separation according to any of the above embodiments, and further separation is performed in the same manner as in the preceding system in the subsequent systems et seq. More preferably, said plural systems are connected in a recycle system. In addition, when the hydrocarbon mixture is separated in the first system according to the embodiment D, E or F, the separation in the next system et seq. is preferably carried out with supplemental feed of new hydrocarbon mixture in the central portion of the band of the residual separated hydrocarbon mixture.

As a further modification of the process, the following process is very effective for separation of a mixture of hydrocarbon isomers:

J. A mixture of hydrocarbon isomers is separated by a process according to any of the above embodiments into the compositions enriched with and depleted in the desired isomer, then the composition depleted in the desired isomer is subjected to isomerization process for conversion to desired isomers and the thus isomerized composition is recycled, if desired, to the separation unit, whereby recovering the composition enriched with the desired isomer in high yield.

In the following, elements of the invention are described in detail.

The term "selectivity" herein used refers to the relative adsorption power of an adsorbent employed for one component over another in the feed hydrocarbon mixture, which is determined by the ratio (W/W) of the adsorbed amount of one component to that of another when equal concentrations of said components are contacted with said adsorbent.

The term "front substance" herein used refers to a substance which is inferior in selectively to an adsorbent employed to any component in the feed hydrocarbon mixture. On the contrary, the term "rear substance" refers to a substance which is superior in selectivity to any component in the feed hydrocarbon mixture.

The feed hydrocarbon mixture

The feed hydrocarbon mixture applicable to this invention is a mixture of two or more hydrocarbon components which have 70° C. or higher critical temperature and 320° C. or lower melting point. Examples of these hydrocarbon components are propane, butane, pentane, hexane, heptane, octane, nonane, decane, dimethyl-pentane, trimethyl-pentane, dimethyl-hexane, and other normal aliphatic hydrocarbons and their isomers; cyclohexane, decaline, tetraline and other alicyclic-hydrocarbons; benzene, toluene, xylene, diethyl-benzene, ethyl-toluene, trimethyl-benzene, butyl-benzene, amyl-benzene, methyl-naphthalene, durene, cumene and other aromatic hydrocarbons such as alkyl-benzene, or alkyl-naphthalene; industrial product of hydrocarbon mixtures of paraffin, naphtha or reformate which may also be called as ultraformer, platformer, hoodleyformer or leniformer; pyrogasoline and other hydrocarbon derivatives from naphtha cracking process, and those products yielded from distillation, alkylation or hydration processes. Both hydrocarbon mixtures comprising two or more compounds of different molecular weights, as well as the same molecular weights, that is, isomers, are included as a feed mixture. Examples of isomer mixtures are $C_8$ aromatic hydrocarbons of paraxylene, meta-xylene, ortho-xylene and ethylbenzene; $C_9$ aromatic hydrocarbons of ethyltoluene and propylbenzene; $C_{10}$ aromatic hydrocarbons of diethylbenzene and butylbenzene; butyl-naphthalene isomers; other aromatic isomers of mono or poly- alkyl-benzene and mono- or poly- alkyl naphthalene; $C_5$ aliphatic isomers of dimethylpropane and pentane; $C_6$ aliphatic isomers of dimethylbutane, ethylbutane, methylpentane and hexane; $C_7$ aliphatic isomers of dimethylpentane, methylhexane and heptane; $C_8$ aliphatic isomers of trimethylhexane and octane; $C_8$ alicyclic isomers of dimethylcyclohexane and ethylcyclohexane.

These hydrocarbon isomers may be hard to separate by ordinary separation method because of their similar chemical or physical properties. On the other hand, some separated isomers are much more important chemical species than their mixtures, such as normal- and isoparaffins, $C_8$ or $C_{10}$ aromatic isomers, for example. The separation process proposed by this invention is effective especially when applied to separate isomers.

There is no practical limit of feed components in this separation process. Very pure product of 99% or more purity can be obtained from an ordinary two or multi-component mixture in which the desired material is of the range between 5 to 95%, or from a very diluted mixture of 1% or lower content by essentially the same steps of separating procedure. Also the same mechanical arrangement according to this invention provides a wide range of desired product, 50% or 99.5% purity, for example, from the same feed mixture of 1% contents.

Another advantage of this invention is that often no change in mechanical arrangement is necessary even when the required purity of the product is shifted.

Adsorbents

According to this invention, adsorbents in the separation process should be so selected that the selectivity of the desired component to the other components are equal to or more than 1.2. It is one of the desirable elements of this process to choose separating conditions and adsorbents to achieve the above selectivity between any set of components which are to be separated into two different groups. In other words, no such restrictions may be necessary when some ingredients in the feed mixture can be allowed to enter the product. The substances to be separated in this specification do not include such ingredients, and only refer to chemical species that must be separated into two different groups.

Generally used inorganic, organic or high-molecular adsorbents are suited for this purpose, as well as the same adsorbents which are specially treated to enlarge the relative adsorption power of the feed mixture. Usually there is some allowance to choose an optimum operating condition to promote the selectivity even with the same adsorbents. The usual procedure of selecting an operating condition is to choose the adsorbent first which can yield high selectivity to the feed components, then to turn to choose front and rear displacement substances.

Inorganic adsorbents suited for the separation processes according to this invention are activated carbons, treated activated carbons, molecular-sieving carbon; selected artificially-synthesized zeolites, such as those having some particular ratio of principal components identified as A, L or X type zeolites, those which have controlled pores of 3 to 30 angstroms, those which have some particular silica-alumina ratio, those in which the original sodium cations are exchanged to other cations; selected silica-gels such as those having some particular relative components of silica, alumina and ferric oxides, those which have particular sterric properties as the average pore diameter, specific surface area, pore volume and others; selected activated alumina such as those having particular components of aluminum oxide and water, those hydrated forms with some particular crystal forms, those which have particular structure; activated clay or selected acid clays such as monotmorillonite in which some base is exchanged, holloysite or attapulgite.

These inorganic adsorbents comprising carbon, silica, alumina, metal oxides, iron, magnesium, hydrated water and/or other elements are characterized as;
  (1) having several different structures, or
  (2) having different components, and
  (3) such that some composing elements are substituted by others, followed by further chemical or physical treatment.

The most suitable adsorbents for a certain feed mixture should be selected from such a wide range of adsorbents groups. Most of the aforesaid adsorbents are readily available in the commercial market. Also the adsorbents similar to those which are commercially available can generally be synthesized without very elaborate technique, or more adsorbents can be prepared by chemically or physically treating commercially available absorbents. It is not difficult to choose a suitable set of adsorbents for a particular feed mixture.

Organic adsorbents include cation-exchange resins with exchange group of benzene sulfonic acid, carboxylic acid, phosphoric acid; strongly or weakly basic anion-exchange resins; high molecular particles of styrene-divinylbenzene copolymer, or its halomethylated, or cyanoethylated polymers; acrylonitrile copolymers; high molecular compounds having several functional groups such as cyano, cyanomethyl, chloromethyl, thioether, sulfone, isocyanate, thiocyanate, thiourea, allyl, acetylacetone, aldehyde, ketone, aliphatic, acid anhydride, ester, halogen, nitro and others.

Composite adsorbents of organic and inorganic material are also suitable for this purpose, some examples of which are complexes of an organic amine such as alkyl pyridine, alkylamine or benzylamine, a metal such as nickel, cobalt, manganese, iron, vanadium, or uranium and an acidic anion of a group such as thiocyanate, cyanate, halogen ion, isocyanate, oxalate or succinate. Example of these complex compounds are 4-methylpyridine-nickel thiocyanate, 4-ethylpyridine-nickel thiocyanate, alkylpyridine-mangnese thiocyanate, alkylpyridine-ferric thiocyanate, benzylamine-nickel thiocyanate, alkylpyridine-manganese chloride. Other composite material of organic compounds with cyano, cyanomethyl, chloromethyl or other functional groups, grafted or adsorbed onto inorganic carriers such as zeolite, silica-gels, acid clay and others may also be included.

The separation effect in this invention can be multiplied by spontaneous repetition of single adsorption-desorption processes as in a batch process of the prior art, when moving an adsorption band of the feed mixture along the developing column. That is, the final product's composition from the batch process of prior art may partly be determined by the number of steps each of which is equivalent to a batchwise separation unit. Whereas, in this invention, the product composition is determined independently of the number of columns, contrary to the batch system. Total separation is achieved according to this invention by summarizing innumerable minute adsorption-desorption processes in each fraction of the adsorption band while moving along the adsorbent bed. Therefore it is essential to keep a much higher rate of absorption-desorption processes relative to the moving rate of the adsorption band for achieving a high degree of separation. The most suitable adsorbents for keeping high adsorption-desorption rates are synthetic zeolites and high molecular weight organic materials. Both adsorbents generally show high exchange rate of moving components, probably because of its chemical affinity to hydrocarbons in case of high weight molecular materials, and because of the macropores in case of synthetic zeolites which comprise minute crystals smaller than a few microns, and clay or other binding material.

Typical example of suitable adsorbents are synthetic zeolite type-A for the separation of normal- and iso-paraffins, type-X or Y or silica gel or complex compound for the separation of aromatic hydrocarbons and silica gel or zeolite or organic adsorbents for the separation of oleffin and naphthene.

Synthetic zeolite is chemically classified as a crystalline alumino-silicate, which is further classified as type A, X, Y, or others by its composition or crystalline forms.

Type A zeolite has a typical oxide formula $Na_2O \cdot Al_2O_3 \cdot 2SiO_2 \cdot 4\frac{1}{2}H_2O$, a typical unit-cell formula $Na_{12}[(AlO_2)_{12}(SiO_2)_{12}] \cdot 27H_2O$, a density of 1.99 g/cc, a unit cell constant of 12.32–24.64 angstroms, a void volume of 0.47 cc/cc, a free aperture of 2.2Å($\beta$)–4.2Å($\alpha$), and a kinetic diameter 3.9–3.6Å.

Type X zeolite has a typical oxide formula $Na_2O \cdot Al_2O_3 \cdot 2.5SiO_2 \cdot 6H_2O$, a typical unit-cell formula $Na_{86}[(AlO_2)_{86}(SiO_2)_{106}] \cdot 264H_2O$, a density of 1.93 g/cc, a unit-cell constant of 25.02–24.86Å, a void volume of 0.50 cc/cc, a free aperture of 2.2Å (6-rings) to 7.4Å (12 rings), and a kinetic diameter of 8.1Å.

Synthetic zeolites are one of the most useful inorganic adsorbents because the adsorption power of hydrocarbons onto zeolites can easily be altered by exchanging sodium ions which usually come from the original production steps into some other cations to change their crystal structure or electron configurations to desired forms. Usually Group I metal ions such as lithium, sodium, potassium, rubidium, cesium; silver, copper; Group II metal ions such as beryllium, magnesium, calcium, strontium, barium; zinc, cadmium, mercury, titanium, vanadium, chromium, nickel, cobalt, iron, manganese, rare earth metals, uranium, lead cations or their mixtures are used to replace sodium ions originally contained in zeolites. The most effective sets of cations are potassium and lithium, potassium and calcium, potassium and cadmium, potassium and iron, potassium and nickel, potassium and cobalt, potassium and barium, potassium and magnesium, calcium and magnesium, calcium and manganese, lithium and manganese, barium and sodium, barium and lead, iron and uranium, and others. Given a particular feed mixture, the most suitable set of cations, their relative compositions, or most effective activation treatments can be easily selected through various experiments, since cation-exchange procedure is readily repeated many times. Generally, the following sets of zeolite and exchanged cations are most effective for give hydrocarbon mixture;

1. Type A synthetic zeolite with calcium ions for separating paraffin isomers, and
2. Type X or Y synthetic zeolites with a set of potassium and one of the cations selected from a group of calcium, lithium, cadmium, iron, nickel, cobalt, barium, magnesium for separating $C_8$ aromatic hydrocarbons.

Front substance

According to this invention, the most suitable front substances for separation of hydrocarbons are compressed gasses such as hydrogen, helium, nitrogen, oxygen, argon, carbon monoxide, carbon dioxide, nitrous oxide, sulfur dioxide and other hydrocarbon gases, such as methane, ethane, propane, butane and others; those substances having dielectric constants of 2.30 or lower at 20° C., such as dimethylpropane, pentane, hexane, dimethyl butane, heptane, cyclopentane, cyclohexane, hexene, carbon tetrachloride, and others.

Rear substance

Suitable rear substances according to this invention are substances having large virial coefficients or those having dielectric constants of 2.30 or higher at 20° C. in liquid phase, the examples of which are water, ammonia, carbon monooxide, carbon dioxide, sulfur dioxide or other inorganic liquids, or organic compounds such as aromatic hydrocarbons, ethers, amino-compounds, esters, halogenated hydrocarbons, ketones, alcohols, acid amines, sulfones, sulfine acids, thioethers and others. Organic rear substances generally used for separation of hydrocarbons are benzene, toluene, xylene, ethylbenzene, diethylbenzene, naphthalene, cumene, durene, diethylether, ethylbutylether, dipropylether, propylethylether, dibutylether, anisole, dioxane, diethylamine, butylamine, ethylenediamine, pyridine, ethylacetate, ethylformate, methylbutyrate, methylvalerate, methylbenzoate, acetone, methylethylketone, butylethylketone, methanol, ethanol, propanol, butanol, benzyl alcohol, aminoethanol, dimethylsulfoxide, epichlorohydrin, furfuryl alcohol, furan, thiol, imidazol, nitromethane, nitroethane, nitrobenzene, acetonitrile, propionitrile, adiponitrile, acetic acid, formic acid, butyric acid, caproic acid, valeric acid, dimethyl sulfone, diethyl sulfone, and others. In embodiments E and F, aromatic hydrocarbons, ethers, amines, halogenated hydrocarbons are desirable. Especially, halogenated hydrocarbons are suited for both rear and front substances, because they are reasonably miscible with the feed hydrocarbons as well as generally yielding good separation effect when used with inorganic adsorbents. Halogenated hydrocarbons with the molecular weight of 190 or lower are most desired for the separation of $C_8$ aromatic hydrocarbons with synthetic zeolites as the adsorbent. The example of these halogenated hydrocarbons is a monohalogenated alkyl compounds expressed as $C_nH_{2n+1}X$ (X denote a halogen atom) in which n is an integer of 10 or less for fluorinate compounds, 8 for chlorinated compounds, 7 for brominated compounds, and 7 for iodinated compounds. Other examples are gem-dihalogenated aliphatic hydrocarbons such as halogenated methylene (e.g. dichloromethylene), halogenated alkylidene (e.g. dichlorobutylene), halogenated ketone; halogenated alkynone, halogenated polymethylene such as dichloroethylene, dichloropropylene; polyhalogenated aliphatic hydrocarbons such as trichloroethane (tetrachloro carbon is excluded); or polyalkyl-polyhalogen compounds. Further examples are epichlorohydrin, dichlorohydrin, ethylenechlorohydrin, dichloroethylether, chloroethyl formate, or halogenated aromatic compounds such as chlorobenzene, fluoro benzene, monochlorotoluene: fluorinated hydrocarbons as identified by the authorized numbers 11, 12, 13, 21, 22, 23, 12b1, 12b2, 111, 112, 113, 114, 115, 121, 122, 122b, 124a, 125, 131c, 132c, 133c, 141a, 142a, 151a, 152, 161, 134c, and others.

The most suitable substances among those halogenated hydrocarbons as enumerated above are chloromethane, dichloromethylene, or chlorinated compounds expressed by the formula;

$$C_nH_{2n+1}Cl \ (n \geq 2)$$

The important point of the separation processes according to this invention is to maintain an adsorption band adsorbed substantially by the feed hydrocarbon mixture onto the adsorbents, in each fraction of which basic separation steps are carried out while moving along the adsobents, as if each fraction act like a minute batch separation unit.

Accordingly, any desired product is obtained independently of the selectivity of the adsorbents in the separation system, by choosing a suitable moving velocity, moving distance between two extractions of product effluent, or other operating conditions. The adsorption band of the feed hydrocarbon mixture should be clearly separated from the surrounding substances by the boundary, one condition of which is that the band comprises substantially only the feed mixture. Desirably the boundary is formed by a clear interface between displacement substances and the feed mixture placed horizontally to the moving direction.

From the microscopic viewpoint, however, the boundary is not a strict interface but a zone in which the feed component and the displacement substance exist together. In other words, three regions are included in the neighbourhood of the macroscopic boundary, i.e. namely regions of the feed components, the displacement substance and the mixture of those two groups of substances. One important condition about the boundary described above is that the mixed zone only contains the desired product components out of the feed hydrocarbon mixture together wth a portion of the displacement substance. Since the object of this invention is to provide the separation processes by adsorbing the feed hydrocarbon mixture within an adsorption band surrounded by the boundary wherein the imaginative multistage separation is made in each fraction of the band, the boundary region should only contain the feed components desired in the product stream.

The adsorption band can be moved through the developing column by feeding a displacement substance or the feed hydrocarbon mixture itself. It is essential in the separation processes according to this invention to move the adsorption band through the developing column; therefore, the displacement substance can not be replaced by other desorbing means such as heating or evacuation, that are common in ordinary separation processes by adsorption.

When the feed mixture is used as a rear substance, it is necessary to choose another substance for the front substance. When a foreign material is used for the rear substance, the feed mixture can be used for the front substance as well as other suitable substances. A typical example of the separation process is to place the adsorption band of a front substance which is relatively less selective to the adsorbents, the adsorption band of the feed mixture, and, the adsorption band of a rear substance which is relatively more selective to the adsorbents in this order and each boundary between two adsorption bands moves in parallel through the developing column (refer FIG. 1 (b)). In this case the clear boundaries are maintained very stably throughout the continuous operation. Another example is a separation process in which the front and the rear substances are same in kind (refer FIG. 1 (c)). In this case the following procedures are necessary to keep the boundaries reasonably clear, that is:
1. The front substance filling the interstitial volume between adsorbent particles should be removed before letting the adsorption band of the feed mixture moving forward against the boundary between the front substance, and/or
2. The boundary region between the adsorption bands of front substance and the feed mixture should be withdrawn periodically as an effluent stream from the developing column, so that a clear, new boundary is formed artificially after each withdrawal.

A typical developing column is a cylinder of 1 cm to 10 m in diameter, equipped with filtering device at top and bottom of the column to prevent the leakage of the adsorbent, or equipped with a distributor connected to the inlet or outlet part of the column. To assure the uniform plug flow through the column or in the auxiliary units around the column, it is necessary to pack the column with the adosorbent particles as uniformly as possible, to finish the inner wall surface of the column smoothly or to reduce the accumulated volume of the auxiliary connecting pipings reasonably smaller than the column volume.

Generally, continuous feed and continuous withdrawal from the column is more favorable than a batchwise operation when practicing the process of separation. This is easily done with only two or more columns being connected in a recycle system one after another. This is another advantage of the separation processes according to this invention compared to the prior art wherein the continuous operation is only achieved with quite a number of columns. This advantage comes from the fact that the adsorption bands of the feed mixture or the developing substances moves in a plug flow.

Figure 2A:
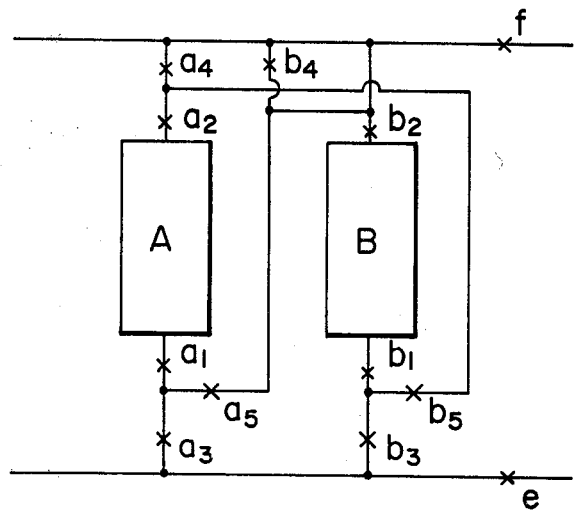
FIG. 2 shows a flow sheet for a typical continuous separating operation, in which A, B and C denote developing columns, and $a_1$–$a_5$, $b_1$–$b_5$, $c_1$–$c_5$, e and f denote the points of connecting pipings to the column, respectively.
Figure 2B:
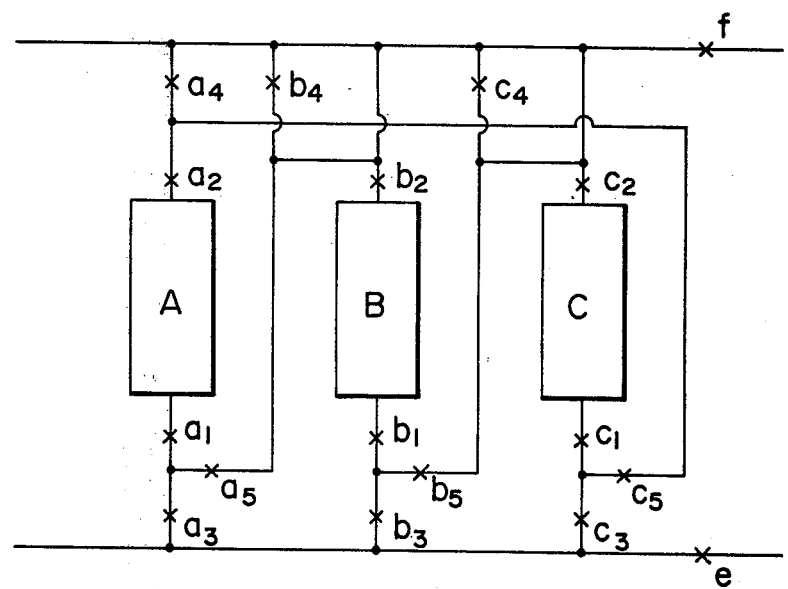

FIG. 2 (b) shows a continuous separation process comprising three successive columns, A, B and C. Each column packed with adsorbents is also full of front substance (FS) and is ready for continuous operation. The feed hydrocarbon mixture (HM) is supplied through the line $e-a_3-a_1$ to column A where HM is adsorbed onto the adsorbent to form an adsorption band separated by a boundary (FB) against the FS. When the boundary FB comes close to the top of the column by feeding HM to column A, the feed mixture supply is suspended. Then, a rear substance (RS) is also supplied through the same line $e-a_3-a_1$ adsorption band RS with a boundary (RB) against the adsorption band of HM. By this procedure three adsorption zones with two boundaries, namely FS zone-boundary FB-HM zone-boundary RB-RS zone, are formed from the top of the column A. Band HM is forwarded to the column C through the line $a_2-c_5-c_1$ as soon as the boundary FB reaches the top of the column A. RS is supplied to the column C through the line $e-c_3-c_1$, after the boundary RB appears in the column C. By this step the adsorption band of the feed mixture is entirely transferred from the column A to the column C. The same procedure is applied and the adsorption band HC is moved from the column C to the column B through line $c_2-b_5-b_1$. In the meantime the adsorption band RS in column A is converted to FS by feeding front substance into the column directly or after removing rear substance by heating or reduced pressure. Repeating this procedure, the adsorption band of HM moves through the columns successively in contact with the adsorption band of FS and the boundary FB in front side, followed by the RS adsorption zone and the boundary RB in rear side. While a row of absorption bands described above moves through the developing column, certain components in the feed mixture begin to accumulate in the vicinity of the front and rear boundaries of the HM adsorption band, and then the accumulation gradually spreads to the middle of the HM adsorption bands as well as the degree of accumulation advances at the both boundaries. Product streams are to be obtained as soon as the desired degree of separation is reached at the both boundaries. Suppose the desired concentration is reached in the column B and the product streams are to be taken out of the outlet of the column.

The steps of feed or extraction of the hydrocarbon mixture are such that; first, a fraction of FB boundary region is taken as a product effluent through the line $b_2-b_4-f$; second, the fraction of front half of the band namely between FB boundary and the middle where the separation is done inadequately is forwarded to the column A through the line $b_2-a_5-a_1$; third, an amount of the feed mixture is supplied to the column A through the line $e-a_3-a_1$ in order to maintain the same band width in the column A; fourth, the fraction of rear half of the band is again forwarded to the column A through the line $b_2-a_5-a_1$ until the rear boundary region where the other feed components are accumulated reaches the upper end of the column B; and finally, another product effluent from the RB boundary region is taken through the line $b_2-b_4-f$. By these successive steps the feed supply and product extraction from the HM adsorption band in the column B are completed, and the fresh band moves ahead in the column A by feeding rear substance through the line $e-a_3-a_1$.

A modified method of this separation process wherein the front substance is the same chemical compound as the rear substance is practically most useful. However, some restrictions exist in the manner of taking product streams from the boundary region. These restrictions come from relatively high adsorption power of the rear substance that causes to broaden the FB boundary when the rear substance adsorbed onto the adsorbents is gradually replaced by the advancing hydrocarbon mixture. In the separation processes according to this invention reasonably clear boundary has to be maintained by avoiding mixing of rear substance into the HM adsorption band. This can be achieved by artifically renewing the FB boundary in the way of taking the whole mixed fraction of the boundary out of the column. That is, for example, the mixed fraction is taken out through the line $b_2$-$b_4$-f when the FB boundary reaches the top of the column B. The following fractions in the HM adsorption band are forwarded to the column A through the line $b_2$-$a_5$-$a_1$ resultantly to form a renewed FB boundary between the RS and HM adsorption bands in the column A. There are some practical ways to reduce mixing at the FB boundary, as follows; first, to take the mixed fraction at the boundary as often as possible; second, to remove rear substance contained in the void volume of the adsorbent particles before developing the HM adsorption band; third, to use an ordinary front substance until the separation within the HM adsorption band reaches its dynamic equilibrium, i.e. until the first product effluent is collected from the column. These methods can be used jointly or independently to obtain a stable clear boundary in the practical applications.

This invention is to provide separation processes in which the product effluent contains essentially high hydrocarbon concentrations. To be more specific, the portion of front or rear substance in the product effluents can be relatively low when the mixing at the boundary is maintained minimum. This is another important advantage of the separation processes according to this invention, compared to the prior art of the selective adsorption in which the product components are usually very diluted by the so-called removing or developing agent. However, distillation, washing or some other procedure may be required to remove the minor portion of the displacement substance in the product stream.

Figure 3:
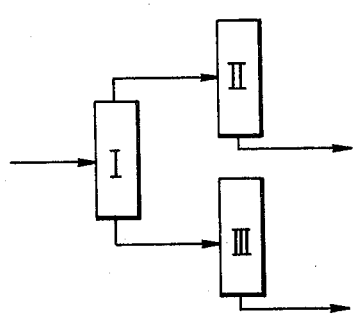
FIG. 3 shows flow diagram of one practical application of the separation process according to this invention, where I denotes the main separation unit for separation of a feed mixture, and II and III units for purification of the separated products such as distillation column.

FIG. 3 shows the basic flow diagram of separation units according to this invention. More simplified flow diagram may be adapted when very different substance, compressed gases for example, is used as a displacement substance.

Figure 4:
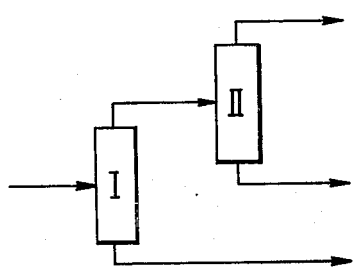
FIG. 4 shows a flow diagram of another application of the separation process according to this invention, when three components in the feed mixture need to be recovered, wherein I and II denote the same main separation units as in FIG. 3.

FIG. 4 shows the basic flow diagram where the feed mixture is separated into three or more components.

Figure 5:
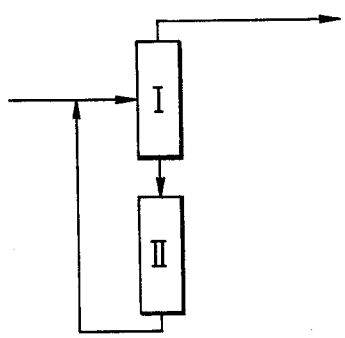
FIG. 5 shows a flow diagram of a modification of the separation process which includes a conversion unit, wherein I denotes the main separation unit and II denotes the conversion unit.

Combination of the separation processes to a conversion unit such as isomerization, decomposition, or others is the most useful method in practical application. FIG. 5 is a basic flow diagram of such combination.

Figure 6:
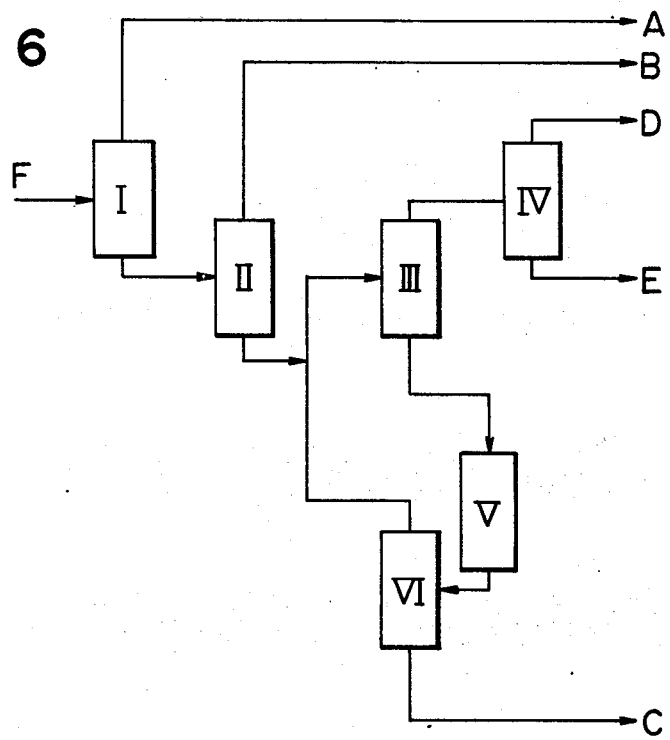
FIG. 6 shows a typical flow diagram of a more complicated combination of the unit processes wherein the components A, B, C, D and E are recovered from the feed mixture, where I, III, IV are the same main separation units as in FIG. 3, II, IV are distillation columns or other recovering unit of feed components from the effluent of the main separation unit, and V is a conversion unit, respectively.

When treating a multi-component feed mixture, this separation process can be skilfully combined with other distillation or conversion units to yield desired products. FIG. 6 shows an example of these complicated flow patterns. The feed mixture F contains the components A, B, C, D, E and M in which the component M can be converted into C, D, and E. The feed mixture F is supplied to the separation column I to obtain the component A. The rest of the feed mixture is treated by the distillation column II. The notations III, IV in FIG. 6 are separation columns devised by this invention, where unit III yields a product stream containing components D and E, which is then treated by unit IV into separate products of D and E, respectively. Unit V is a conversion process which is applied to the components M or those other than C yielding C, D or E. The component C is extracted from the feed mixture in Unit V, and the rest is recycled to column II.

Following effects are to be realized by practicing the separation processes according to this invention, that is;
1. A product stream of arbitrary composition can be obtained independently to the relative adsorption power of each component onto the adsorbents;
2. Very high degree of purification is achieved;
3. Product streams are not very diluted by displacement substances or other foreign materials;
4. In some cases a product stream comprising solely a part of the feed components is obtained;
5. No particular arrangement for the mechanism of the separation process is required;
6. Simple operation steps can be employed; and others.

EXAMPLE 1

A jacketed development column of 8 mm. in diameter and 600 cm. in length, which had filters at top and bottom of the column, was packed with adsorbents of a lithium- and potassium-substituted Y-type zeolite having an average particle diameter of 105 microns. As the front substance was used nitrogen gas, as the rear substance was used methylene chloride, and as the hydrocarbon mixture was used a mixture comprising 20% p-xylene, 40% m-xylene, and 40% o-xylene.

The front substance, the $C_8$ isomer mixture and the rear substance were introduced in this order in a plug flow through the bottom of the column under the conditions of a development temperature of 50° C., a development pressure of 1.2 kg/cm$^2$ and a boundary displacement rate of 7.5 m/hr.

The development was performed while forming a front boundary and a rear boundary in the column, and the effluent flowing out through the top of the column was recovered in 2 ml fractions.

The purity of the fraction No. 1 from the front boundary, in terms of the percentages between $C_8$ isomers, was 99.992% of m-xylene and o-xylene. The purity of the fraction No. 1 from the rear boundary was 99.995% of p-xylene.

EXAMPLE 2

A cylindrical development column of 30 mm. in diameter and 1100 mm. in length was packed with an adsorbents of X-type zeolite. The temperature and the pressure in the column were controlled to 150° C. and 5.2 kg/cm$^2$.

After the nitrogen gas was charged to the column, a mixture comprising 5% n-octane, 23% benzene, 51% xylene and 21% toluene was introduced in a plug flow to the column and the front boundary displacement rate was controlled to 0.5 m/hr.

The fractions of each 2 ml. from the top of the column, after about 2 hours, were recovered and analyzed. As the result, the n-octane purity of the fraction No. 1 was 99.92%.

EXAMPLE 3

A cylindrical development column of 10 mm. in diameter and 400 cm. in length, which had upper and lower filters, was packed with adsorbents of a synthetic zeolite having an average pore diameter of 9 Å and an average volume particle diameter of 223 microns, and the temperature inside the column was controlled to 30° C. As the front substance was used nitrogen gas, and as the hydrocarbon mixture was used a mixture comprising 20 wt% of benzene and 80 wt% of p-xylene. In this case, the selectivity of p-xylene to benzene was 2.5. The mixture was introduced in a plug flow through the bottom of the column, and was displaced at a boundary rate of 500 cm/hr while forming in the column a boundary with nitrogen gas. Each 2.0 ml. of effluents from the column top were recovered and analyzed. As the result, the benzene purities of individual liquids in the order recovered from the boundary were 99.9%, 99.4%, 99.2% 99.0%, 90.5%, 81.2%, 77.3%, 62.1%, 55.5% and 33.2%, respectively.

EXAMPLE 4

A jacketed cylindrical development column of 30 mm. in diameter and 400 cm. in height, which had filters and tapered inlets at top and bottom, was packed with adsorbents of a synthetic zeolite having an average pore diameter of 10 Å, a structure of (Na, Ca, Mn) $O.Al_2O_3.2.5SiO_2$ (wherein the ratio of Na:Ca:Mn was 0.2:0.5:0.3) and an average volume particle diameter of 250 microns. As the front substance was used n-propane, and as the hydrocarbon mixture was used a mixture comprising 50% of p-xylene and 50% of m-xylene. In this case, the selectivity of m-xylene to p-xylene was 5.97. In the same manner as in Example 3, the mixture was introduced in a plug flow through the bottom of the column and displaced at a boundary rate of 800 cm/hr at a development temperature of 150° C., and each 2.0 ml. of the effluent from the top of the column were recovered. As the result, the fraction No. 1 from the boundary contained 99.15% of p-xylene, and the fraction No. 2 99.32% of p-xylene. Thus, 4.0 ml. of 99.5% or more of desired p-xylene was obtained.

EXAMPLE 5

A jacketed cylindrical development column of 30 mm. in diameter and 10 m. in height, which had filters and tapered inlets, was packed with adsorbents having an average volume particle diameter of 80 microns which had been prepared by chloromethylating a styrene-divinylbenzene copolymer. As the front substance was used nitrogen gas, and as the hydrocarbon mixture was used a mixture comprising 50% of 3-methylpentane and 50% of 1-hexene. 3-Methylpentane has a boiling point of 63.282° C. and 1-hexene has a boiling point of 63.485° C., but the selectivity of 1-hexene to 3-methylpentane was 1.41. Development was performed at a temperature of 42° C., a boundary displacement rate of 23 cm/hr and an inner pressure of 1.2 kg/cm$^2$, and 1.0 ml. of top effluent was recovered to obtain a composition containing 92.2% of 3-methylpentane.

EXAMPLE 6

A cylindrical development column of 8 mm. in diameter and 100 cm. in height, which had filters, was packed with an adsorbent prepared by treating with an aqueous nickel thiocyanate solution a globular resin obtained by copolymerization of 4-vinylpyridine with divinylbenzene and then drying the treated resin. As the front substance was used n-heptane, and as the hydrocarbon mixture was used a low purity divinylbenzene mixture comprising 45% of ethylvinylbenzene and 55% of divinylbenzene. Development was performed at a development temperature of 22° C. and a boundary displacement rate of 8.9 m/hr. In this case, the selectivity of ethylvinylbenzene to divinylbenzene was 1.89. After the development, 3.5 ml. of a composition containing 90% or more of divinylbenzene was obtained as a part of the effluents.

As will be seen from the results in the above Examples 3 to 6, a selected composition can be recovered according to the simplest embodiment of the process by easy operations as in the case of batch process of prior art even if the selectivity of the components in the hydrocarbon mixture is close to 1.

EXAMPLE 7

A jacketed cylindrical development column of 10 mm. in diameter and 50 cm. in length was packed with an adsorbent having an average pore diameter of 10 Å and an average volume particle diameter of 350 microns which was an X-type zeolite having a structure of $0.9Na.Al_2O_3 2.5SiO_2.7H_2O$. As the front substance was used nitrogen gas, as the rear substance was used pyridine, and as the hydrocarbon mixture was used a mixture comprising 19.5 wt% of benzene and 80.5 wt% of 2,4-dimethylpentane. Development was performed at a development temperature of 90° C., a development pressure of 2.7 kg/cm$^2$ and a boundary displacement rate of 1 m/hr. The introduction of the fluids are carried out in such a manner that the front substance, the mixture and the rear substance were introduced in this order in a plug flow through the bottom of the column, and development was conducted to form front and rear boundaries in the column. From the front boundary were recovered each 0.5 ml. of five fractions, while from the rear boundary were recovered each 0.5 ml. of five fractions. The composition in the first fraction recovered from the front boundary was 99.85% of dimethylpentane and 0.15% of benzene, and that in the first fraction recovered from the rear boundary, which contained 8% of rear displacement agent, was 99.23% of benzene and 0.77% of dimethylpentane.

EXAMPLE 8

Development was performed in a jacketed cylindrical development column of 30 mm. in diameter and 90 cm. in length which had upper and lower filters. As the adsorbent was used granular adsorbents prepared by cyanomethylating a styrene-divinylbenzene-acrylonitrile copolymer. The adsorbent has, as measured by means of a mercury-injecting type pore diameter-measuring apparatus, an average pore diameter of 240 Å, a specific surface area of 220 m$^2$/g, a pore diameter distribution of 90% between 140 Å and 320 Å, an apparent specific gravity of 0.34 g/ml, and an average particle diameter of 82 microns. As the hydrocarbon mixture was used a mixture comprising 98% of toluene, 1% of a dimethylhexane isomer mixture and 1% of a trimethylpentane isomer mixture, as the front substance was used n-nonane, and as the rear substance were used four kinds of compounds, namely n-butyl ethyl ether, isobutyl ethyl ether, secondary butyl ethyl ether and tertiary butyl ethyl ether, and the development was conducted 4 times by varying the rear substance. In each development, the n-nonane, the toluene mixture, and each rear substance were introduced in this order in a plug flow through the top of the column, and the rear boundary was recovered from the bottom of the column. As the result, the composition recovered from the rear boundary by use of the respective rear substances employed, when represented by the purity of toluene after removal of ether by distillation, were 99.98% with n-butyl ethyl ether, 99.21% with isobutyl ethyl ether, 99.39% with secondary butyl ethyl ether, and 99.28% with tertiary butyl ethyl ether. In this example, the selectivity of toluene to impurities in toluene was 1.5 or more, that to the front substance was 3.0 or more, and that to each rear substance was 3.0 or less.

EXAMPLE 9

Two jacketed cylindrical development columns of 10 mm. in diameter and 300 cm. in length were prepared. In the first column was used as adsorbent a synthetic zeolite having an average pore diameter of 10 Å, a packed density of 750 g/L, and a chemical composition of $(Na, K)O.Al_2O_3.2.5SiO_2$. Further, in each of the two columns, nitrogen gas was used as the front substance, and ethyl alcohol as the rear substance. As the hydrocarbon mixture, there was used in the first column a mixture of aliphatic hydrocarbons consisting of 12.7% of heptane and 31.8% of hexane and aromatic hydrocarbons consisting of 6.9% of benzene, 25.3% of toluene and 23.3% of $C_8$ aromatic isomers. The development was conducted under conditions of a temperature of 80° C. and a boundary displacement rate of 5.3 m/hr. Throughout the columns, the selectivity of the front substance to any of the components of the substance to be separated was 10 or less, and that of the rear substance to any of the components of the mixture was 10 or more. Further, in the first column, the selectivity of both p-xylene and ethylbenzene to any of heptane, hexane, benzene, toluene, m-xylene and o-xylene were 1.5 or more, while in the second column, the selectivity of both m-xylene and o-xylene to any of heptane, hexane, benzene and toluene were 1.6 or more.

In the first place, the front substance, the hydrocarbon mixture and the rear substance were introduced in a plug flow in this order into the first column and development was carried out at the boundary displacement rate of 5.3 m/hr. From the front boundary was recovered as effluent a fraction composed of p-xylene and 1% or less of ethylbenzene, and from the rear boundary was recovered as effluent a fraction composed of p-xylene and 99% or more of ethylbenzene. The fractions from the front boundary were successively used as the feed in the second column. The development conditions and operations in the second column were entirely the same as those in the first column. After development in the second column, a composition comprising a total of 99% of heptane, hexane, benzene and toluene was obtained from the front boundary, and a composition comprising a total of 98% of m-xylene and o-xylene was obtained from the rear boundary.

EXAMPLE 10

A jacketed cylindrical development column of 20 mm. in diameter and 100 cm. in length was packed with an adsorbent, which was globular silica gel having an average pore diameter of 21 Å and an adsorptive surface area of 625 m²/g. As the front substance was used carbon dioxide, as the rear substance was used ethyl alcohol, and as the hydrocarbon mixture was used a mixture comprising 15.9% of $C_5$ aliphatic hydrocarbons, 9.0% of $C_6$ aliphatic hydrocarbons, 4.5% of $C_7$ aliphatic hydrocarbons, 5.5% of $C_8$ aliphatic hydrocarbons, 1.8% of aliphatic hydrocarbons having 9 or more carbon atoms, 29.5% of benzene, 17.7% of toluene, 9.3% of $C_8$ aromatic hydrocarbons, and 6.8% of aromatic hydrocarbons having 9 or more carbon atoms. The selectivity of the aromatic hydrocarbons to the aliphatic hydrocarbons was 5.71, and the highest selectivity among the aromatic hydrocarbons was 1.48. Development was performed at a development temperature of 113° C., a development pressure of 4.2 kg/cm², and a boundary displacement rate of 2.5 cm/hr. The starting material was composed of 36.7% of aliphatic hydrocarbons and 63.3% of aromatic hydrocarbons. After the development, 5 ml. of the front boundary fraction and 6 ml. of the rear boundary fraction had compositions of 98.5% of aromatic hydrocarbons and 97.3% of aliphatic hydrocarbons, respectively.

EXAMPLE 11

A cylindrical development column of 10 mm. in diameter and 300 cm. in length was packed with an adsorbent prepared by subjecting silica gel having an average pore diameter of 23 Å and an adsorptive surface area of 650 m²/g to reaction with trimethoxysilane. The treated silica gel had sufficiently been washed with toluene to completely remove the silane treating agent. As the front substance was used ethane, as the rear substance was used acetonitrile, and as the hydrocarbon mixture was used a mixture comprising 50% of cyclohexane and 50% of cyclohexene. Development was performed at a temperature of 180° C., a pressure of 10.8 kg/cm², and a displacement rate of 25 cm/hr, and 1 ml. fraction was recovered from the front boundary and 1 ml. fraction from the rear boundary. The fractions were analyzed to obtain 99.8% of cyclohexane from the front and 98.1% of cyclohexene from the rear.

EXAMPLE 12

A cylindrical development column of 10 mm. in diameter and 100 cm in length was packed with 1/16-inch pellets of an L-type synthetic zeolite composed of $K_2O.3.0SiO_2.Al_2O_3.1.5H_2O$. As the front substance was used helium, as the hydrocarbon mixture was used a mixture comprising 50% of cyclopentane and 50% of 2,2-dimethylbutane, and as the rear substance was used ethyl ether. Since the boiling point of 760 mmHg. of cyclopentane is 49.262° C. and that of 2,2-dimethylbutane is 49.741° C., it was difficult to separate the said compounds by distillation. Furthermore, since the melting point of the former compound is −93.866° C. and that of the latter compound is −99.865° C., the separation of said compounds by deep cooling was also difficult. Moreover, the said compounds are similar in chemical properties, and hence had no such selectivity as could be separated by batch process of prior art. The selectivity onto the adsorbent used in this Example of 2,2-dimethylbutane to cyclopentane was 1.23. According to the batch process of prior art, the operation consisting of adsorption of a mixture of cyclopentane and 2,2-dimethylbutane, desorption of the adsorbed mixture and removal of the desorbent should be repeated for many cycles. For example, 23 cycles of said operation were required for the production of 98% or more of cyclopentane. In contrast, when the development was performed according to the present process at 25° C., 1.0 atm., and a boundary displacement rate of 2.1 cm/hr, 99.4% of cyclopentane was obtained from the front boundary of the first effluent and 98.2% of dimethylbutane from the rear boundary, respectively, by one step operation.

EXAMPLE 13

A jacketed cylindrical development column of 10 mm. in diameter and 5,000 mm. in length, which had filters and tapered inlets at the top and bottom of the column, was packed with a granular substance having an average volume particle diameter of 152 microns. The said granular substance was a synthetic zeolite having an average pore diameter of 10 Å and a structure of $Me_{86}(SiO_2)_{106}(Al_2O_3)_{86}(H_2O)_{264}$ (where Me represents the total amount of metals) which had been substituted by magnesium, calcium and vanadium, and then drying the grafted zeolite at 100° C. for 90 hours under 10 mmHg. As the starting material was used a mixture comprising 30% of p-xylene and 70% of m-xylene, as the front substance was used nitrogen gas, and as the rear substance was used 1,4-dioxane. In this case, the selectivity of m-xylene to p-xylene was 3.51, nitrogen gas had little adsorption, and the selectivity of 1,4-dioxane to m-xylene was 8.2.

The development column was packed with the adsorbent and filled with nitrogen gas. The inner temperature of the column was controlled to 120° C., 90 g. of the xylene isomer mixture preheated to 120° C. was introduced into the column, and, successively, 1,4-dioxane was continuously introduced through the bottom of the column. In this case, the front boundary rate in the column was controlled to 1.2 m/hr. Effluents of xylene from the top of the column were recovered in 45 fractions (2 g. per each fraction). As the result, the fraction from the front boundary was composed of 99.92% of p-xylene and 0.08% of m-xylene, and the fraction from the rear boundary was composed of 1.20% of p-xylene, 69.22% of m-xylene and 29.58% of 1,4-dioxane.

EXAMPLE 14

A jacketed cylindrical development column of 30 mm. in diameter and 90 cm. in length, which had filters at the top and bottom of the column, was packed with a granular substance having an average particle diameter of 53 microns. The said granular substance had been prepared by grafting 1.3% of a chloroethyl group on a synthetic zeolite having an average pore diameter of 12 Å and a structure of $Me_{86}(SiO_2)_{106}(Al_2O_3)_{86}(H_2O)_{264}$ (where Me represents the total amount of metals) which had been substituted by potassium, silver, barium and uranium, and then heating the grafted zeolite at 350° C. for 8 hours under atmospheric pressure. As the starting material was used a mixture comprising 20% of p-xylene, 40% of m-xylene, 20% of o-xylene and 20% of ethylbenzene. As the front substance was used n-heptane, and as the rear substance was used methanol. In this case, the selectivity of p-xylene to m-xylene was 5.5, that to o-xylene 6.4 and that to ethylbenzene 8.9. The selectivity of each of p-xylene, m-xylene, o-xylene and ethylbenzene to n-heptane was 3.0 or more and that to methanol 3.0 or less. The development in the column was carried out at 112° C. in such a manner that the front substance, the isomer mixture and the rear substance were introduced in this order in a plug flow into the column. The rate of displacement of the rear boundary was controlled to 2.8 m/hr, and each 1 ml. of effluents from the top of the column were recovered. From the boundary with the front substance was obtained the fraction containing 99% or more of the total of m-xylene, o-xylene and ethylbenzene, and from the boundary with the rear substance was obtained the fraction containing p-xylene and methanol. The mixture was further subjected to distillation to separate xylene, whereby 98.1% or more of p-xylene was obtained.

EXAMPLE 15

A jacketed cylindrical development column of 30 mm. in diameter and 90 cm. in length, which had filters at top and bottom, was packed with pellets (16 mm.) of synthetic mordenite having a pore diameter of 7.0 Å and a structure of $Na_8(SiO_2)_{40}(Al_2O_3)_8(H_2O)_{22}$. As the hydrocarbon mixture was used a 1:1 mixture of p-diethylbenzene and m-diethylbenzene, as the front substance was used propane, and as the rear substance was used pyridine. The front substance, the hydrocarbon mixture and the rear substance were introduced in a plug flow through the bottom into the column packed with the adsorbent, which had completely been dried. The selectivity at 180° C. between the components of the hydrocarbon mixture was 1.58. Development was performed while maintaining a boundary displacement rate of 39 cm/hr, and each 1 ml. of fractions of effluent from the top of the column were recovered. As the result of analysis, m-diethylbenzene having a purity of 98.2% was obtained from the front boundary and p-diethylbenzene having a purity of 99.1% from the rear boundary.

EXAMPLE 16

A development column, having at bottom a filter, of 20 mm. in diameter and 100 cm. in length was packed with an adsorbent having an average pore diameter of 10 Å and an average volume particle diameter of 350 microns. The adsorbent was a Y-type zeolite having a structure of $Me_{56}(SiO_2)_{136}(Al_2O_3)_{56}(H_2O)_{250}$ (where Me represents the total amount of metals) which had been substituted by potassium. As the front substance was used propane gas, as the rear substance was used nitromethane, and as the hydrocarbon mixture was used a $C_8$ isomer mixture comprising 50% of ethylbenzene and 50% of p-xylene. The front substance, the $C_8$ isomer mixture and the rear substance were introduced in this order in a plug flow through the bottom of the column under the conditions of a development temperature of 40° C., a development pressure of 1.0 kg/cm$^2$ and a boundary displacement rate of 71 cm/hr. The development was carried out while forming a front boundary and a rear boundary in the column, and effluents from the top of the column were recovered in fractions of each 2.0 ml. From the front boundary were obtained the first fraction containing 99.8% of ethylbenzene, the second fraction containing 99.2% of ethylbenzene, the third fraction containing 91.7% of ethylbenzene and the fourth fraction containing 82.8% of ethylbenzene. From the rear boundary were obtained the first fraction contaning 99.5% of p-xylene, the second fraction containing 99.5% of p-xylene, the third fraction containing 95.3% of p-xylene and the fourth fraction containing 84.3% of p-xylene. Further, the ratio of the front substance contained in the combined fractions having an average concentration of 99.5% was as little as 1.2% and that of the rear substance 19.8%.

EXAMPLE 17

A jacketed development column of 8 mm. in diameter and 500 cm. in length, which had a lower filter, was packed with adsorbents of a lithium- and calcium-substituted Y-type zeolite having an average pore diameter of 8 Å and an average volume particle diameter of 170 microns. As the front substance was used nitrogen gas, as the rear substance was used ethane chloride, and as the hydrocarbon mixture was used a $C_8$ isomer mixture comprising 22.0% of ethylbenzene, 17.9% of p-xylene, 40.1% of m-xylene and 20.0% of o-xylene. The front substance, the $C_8$ isomer mixture and the rear substance was introduced in this order through the top of the column under the conditions of a development temperature of 50° C., a development pressure of 4 kg/cm$^2$ and a boundary displacement rate of 125 cm/hr. The development was performed while forming a front boundary and a rear boundary in the column, and the effluent from the bottom of the column was recovered in fractions of each 1 ml. The purity of the fraction from the front boundary, in terms of the percentages between $C_8$ isomers, was 63.0% of ethylbenzene, 36.9% of p-xylene, and 0.1% of the total of m-xylene and o-xylene. The purity of the fraction from the rear boundary, in terms of the percentages between $C_8$ isomers, was 63.4% of m-xylene, 36.4% of o-xylene, and 0.2% of the total of ethylbenzene and p-xylene.

EXAMPLE 18

A development column (having a lower filter) of 20 mm. in diameter and 100 cm. in length was packed with adsorbents of a potassium substituted X-type zeolite having an average pore diameter of 10 Å and an average volume particle diameter of 350 microns. As the front substance was used propane, as the rear substance was used fluorobenzene, and as the hydrocarbon mixture was used a $C_8$ isomer mixture comprising 50% of ethylbenzene and 50% of p-xylene. The front substance, the $C_8$ isomer mixture to be separated and the rear substance were introduced in this order through the bottom of the column under the conditions of a development temperature of 150° C., a development pressure of 1.2 kg/cm$^2$ and a boundary displacement rate of 38 cm/hr, and development was performed while forming a front boundary and a rear boundary in the column. The effluent from the top of the column was recovered in fractions of each 2.0 ml. The purities of the fractions No. 1 to No. 4 from the front boundary contained 99.2%, 98.3%, 89.5% and 80.1% of ethylbenzene, respectively. The purities of the fractions No. 1 to No. 4 from the rear boundary contained 99.6%, 99.4%, 96.2%, and 81.5% of p-xylene, respectively. The ratio of displacement agent contained in combined fractions having an average concentration of 99.5% or more was as little as 1.2% in the case of the front boundary, and was 5.3% in the case of the rear boundary.

EXAMPLE 19

A cylindrical development column of 10 mm. in diameter and 100 cm. in height was packed with adsorbents of an X-type zeolite, 35.2% of which had been substituted by Cd. As the front substance was used heptane, and as the hydrocarbon mixture was used a mixture comprising 50% of ethylbenzene and 50% of o-xylene, and development was performed at a development temperature of 92° C., a development pressure of 2.1 kg/cm$^2$ and a boundary displacement rate of 35 cm/hr. In this case, the selectivity of ethylbenzene to o-xylene was 2.44. Further, methylene chloride, ethylenediamine, n-butyl ethyl ether, methyl alcohol, nitromethane and acetonitrile was used as the rear substance. In each case, the feed mixture was introduced through the bottom of the column, and effluents from the top of the column were recovered in fractions of each 0.5 ml.

In Table 1, there were shown the ethylbenzene concentration (mark EB%) of the front boundary and the o-xylene concentration (mark OX%) of the rear boundary, and the ratio of rear substance contained in the rear boundary composition was represented by the ratio to 1.00 of $C_8$ compound (mark RS (r)).

Table 1

| Rear substance | EB % | OX % | RS (r) |
|---|---|---|---|
| Methylene chloride | 99.89 | 99.90 | 0.03 |
| Ethylenediamine | 99.87 | 98.24 | 0.12 |
| n-Butyl ethyl ether | 99.91 | 98.61 | 0.17 |
| Methyl alcohol | 99.85 | 97.02 | 0.22 |
| Nitromethane | 99.85 | 97.35 | 0.06 |
| Acetonitrile | 99.90 | 97.11 | 0.08 |

EXAMPLE 20

A cylindrical development column of 30 cm. in diameter and 300 cm. in height was packed with adsorbents of an L-type zeolite, 53.1% of which had been substituted by Ba. As the front substance was used ethane, as the hydrocarbon mixture was used a mixture of equal amounts of p-xylene and m-xylene, and as the rear substance was used methane chloride. Development was performed at a development temperature of 30° C., a development pressure of 15 kg/cm$^2$ and a displacement rate of 200 cm/hr. From the front boundary was recovered 40 ml. fraction, and from the rear boundary also 45 ml. fraction. These fractions were analyzed to find that the front boundary fraction contained 99.8% of m-xylene, and the rear boundary fraction contained 99.7% of p-xylene and 5 ml. of methane chloride. The rear boundary liquid was brought back to normal pressure, whereby the methane chloride was evaporated to give 40 ml. of pure $C_8$ composition.

The results in Examples wherein the process of the present invention is applied to the separation of $C_8$ aromatic isomers show that the separation efficiency at the front boundary is identical with that at the rear boundary, and there are obtained such advantages that (1) the amount of the displacement substance per unit separation amount is small, (2) separated $C_8$ aromatic isomers can be obtained at high concentrations, (3) the operation is quite easy, (4) so far as the selectivity is 1.2 or more, any desired composition can be obtained from any composition of the starting material to be separated, and (5) the desired composition can be varied by merely varying the operational conditions.

In the following Examples, a displacement substance and a feed mixture are charged alternately to form front and rear boundaries at both sides of the adsorption band.

EXAMPLE 21

There were used two jacketed cylindrical development columns of 10 mm. in diameter and 1,000 mm. in length, each of which had tapered inlets and filters at the top and bottom of the column. The development columns and their piping were as shown in FIG. 2 (a). As the absorbent was used a synthetic zeolite having an average diameter of 9 Å and a structure of $(Cd)_{86}(SiO_2)_{106}(Al_2O_3)_{86}(H_2O)_{264}$, 73% of which had been substituted by cadmium. The zeolite was a granular material having an average volume particle diameter of 0.53 mm., and was used after drying and activation. As the starting material was used a mixture comprising 20% of ethylbenzene, 20% of o-xylene, 40% of m-xylene and 20% of p-xylene, as the front substance at the time of initiation of operation was used nitrogen gas, and as the rear substance was used propyl ethyl ether. The selectivities of o-xylene, m-xylene and p-xylene to ethylbenzene at a development temperature of 130° C. and a development pressure of 1.5 kg/cm² were 4.3, 4.8 and 1.03, respectively.

The average plug flow rate in the column was controlled to 1 m/hr in terms of linear velocity, and the operation was initiated according to FIG. 2 (a). At the time of initiation of the operation, both the columns A and B packed with adsorbents were filled with nitrogen gas, and adjusted to the development conditions. The hydrocarbon mixture (HM) was introduced through the route of (e-$a_3$-$a_1$) to form a front boundary in the column A, and was further introduced. When the front boundary reached the top of the column A, the rear substance (RS) was introduced through the same route as above. From the column A, the adsorption band was transferred through the route of ($a_2$-$b_5$-$b_1$), to the column B wherein the development was continued with the same flow until the front boundary reached the top of the column B. At this stage, the route of introduction of RS was changed to (e-$b_3$-$b_1$), and the route of ($b_2$-$a_5$-$a_1$) from the top of the column B was opened, while the route of ($a_2$-$a_4$-f) was opened and was used as an outlet for RS in the column A. With progress of the development, the rear boundary reached a steady state and displaced while forming a favorable boundary in the column B, while the front boundary was kept in contact with the front substance. At the initial operation, the state inside the columns A and B was favorable, but in the column A at the subsequent operation which was conducted in repeated cycles, it was observed that RS gradually migrated into the adsorption band.

The development was performed as it was, i.e. while maintaining the whole flow of (e-$b_3$-$b_1$-$b_2$-$a_5$-$a_1$-$a_2$-$a_4$-f), until the front boundary reached the top of the column A, and the desired composition in the vicinity of the front boundary was recovered. Immediately thereafter, the route was changed to the route of ($a_2$-$b_5$-$b_1$), and RS was introduced through (e-$a_3$-$a_1$). The desired composition at the initial operation from the front boundary was obtained in twenty fractions of each 0.3 ml. As the result, the total of ethylbenzene and p-xylene among the isomers having 8 carbon atoms was 99% or more in the combined fractions. RS was detected in the fraction Nos. 1 to 13 but was not detected in fraction Nos. 14 to 20. It was observed that the front boundary, which had been introduced through ($a_2$-$b_5$-$b_1$) into the column B, had formed a fresh, favorable boundary. The development was conducted while introducing the starting material through (e-$b_3$-$b_1$) and recovering the desired composition of the rear boundary through ($a_2$-$a_4$-f). When the front boundary reached the top of the column B, the desired composition was recovered through ($b_2$-$b_4$-f) in fractions of each 0.3 ml. As the result of analysis, it was found that the concentration of ethylbenzene and p-xylene based on the total amount of the feed mixture was 99% or more, and no RS was entrained therein before the fraction No. 10. In this manner, the desired compositions were recovered from the front and rear boundaries each ten times from the columns A and B. As the result, the amount of the displacement substance entrained in the fractions from the front boundary, the ratio between isomers in said fractions, the amount of the displacement substance entrained in the fractions from the rear boundary, and the ratio between isomers in said fraction were substantially constant in every time of the repeated operations.

EXAMPLE 22

Example 21 was repeated, except that the adsorbent used was a synthetic zeolite having an average pore diameter of 9 Å and a structure of $(K)_{86}(SiO_2)_{106}(AlO_2)_{86}(H_2O)_{264}$, which had been substituted by potassium (a granular material having an average volume particle diameter of 0.38 mm. and dried and activated before use) and that the rear substance used was dichloromethane. The selectivities of o-xylene, m-xylene and p-xylene to ethylbenzene onto the adsorbents at a development temperature of 40° C., and a development pressure of 1.5 kg/cm² were 0.3, 0.6 and 2.1 respectively.

The results obtained were similar to those in Example 24 except that RS was detected in fraction Nos. 1 to 7 and not in fraction Nos. 8 to 20 in the composition from the front boundary and that no RS was detected before the fraction No. 10 in the composition from the rear boundary.

EXAMPLE 23

There were prepared three jacketed cylindrical development columns of 30 mm. in diameter and 100 cm. in length, each of which had filters and distribution means as inlets at the top and bottom of the column. These columns were assembled by use of valves and pipes as seen in FIG. 2 (b). As the adsorbent was used a sodium type zeolite having an average pore diameter of 8 Å which was of the Faujasite type when viewed from the crystallography. As the starting material was used a distillate obtained by fractionating a mixture of reformates from petroleum naphtha which had contained hydrocarbons with 6 to 8 carbon atoms as principal components, and then recovering fractions distilled at 95° to 124° C. The composition of the distillate was 48% of toluene and 52% of a non-aromatic mixture. At the time of initiation of development, all the columns A, B and C were filled with nitrogen gas, and as the rear substance was used diethylamine. Thus, the initial development proceeded while forming boundaries. In subsequent cycles after the initial development, the columns A, B and C were repeatedly used and each of said columns had been filled with diethylamine as front substance. As the result, the penetration of diethylamine into the adsorption band of the hydrocarbon mixture was observed in the front boundary. However, the portion of adsorption band, into which diethylamine had already penetrated, was removed as desired composition thereby to be replaced by fresh diethylamine, whereby there was newly formed an artificial boundary free from mutual penetration. The stage, at which the operation could thus be repeated stably, could be regarded as a steady state.

After the steady state, a composition comprising 18% of a hydrocarbon mixture enriched with non-aromatics and 82% of the rear substance, which hydrocarbon mixture was composed of 98% of non-aromatic compounds and 2% of toluene, was obtained from the front boundary, while a composition comprising 27% of a toluene-rich hydrocarbon mixture and 73% of the rear substance, which hydrocarbon mixture was composed of 99.2% of toluene and 0.8% of nonaromatic compounds, was obtained from the rear boundary.

EXAMPLE 24

Example 23 was repeated except that dichloroethane was used in place of diethylamine as the rear substance.

After the steady state, a liquid comprising 18% of a hydrocarbon mixture enriched with non-aromatics and 82% of the rear substance, which hydrocarbon mixture was composed of 98% of non-aromatic compounds and 2% of toluene, was obtained from the front boundary, while a liquid comprising 62% of a toluene-rich hydrocarbon mixture and 38% of the rear substance, which hydrocarbon mixture was composed of 99.2% of toluene and 0.8% of non-aromatic compounds, was obtained from the rear boundary.

EXAMPLE 25

There were used jacketed cylindrical development columns of 10 mm. in diameter and 2,000 mm. in length, each of which had filters and tapered inlets at the top and bottom of the column. The development columns are arranged in the same manner as in Example 24.

As the adsorbent was used a synthetic zeolite, which was a granular material having a particle diameter of 100 to 150$\mu$ and a structure of $Na_{56}[(AlO_2)_{56}(SiO_2)_{136}]250H_2O$. The adsorbent was subjected to ion exchange by contact with 10 or more times the exchange capacity thereof of an aqueous solution containing 20% and 3% (by weight) of potassium chloride and barium chloride, respectively, to control residual sodium in the adsorbent to 0.5% or less. After the ion-exchange, the adsorbent was washed with water, dried at 500° C., activated before use. As the starting material was used a mixture comprising 20% of ethylbenzene, 20% of o-xylene, 40% of m-xylene and 20% of p-xylene, and as the displacement substance was used ethyl chloride. At the time of initiation of operation, ethyl chloride was present at the adsorptive portion of the adsorbent in the development column, and nitrogen gas was present at the non-adsorptive portion. The operation was initiated according to FIG. 2 (a) at a development temperature of 40° C. and a development pressure of 15 kg/cm$^2$, while controlling the average plug flow rate in the column to 1.5 m/hr in terms of linear velocity. In the first place, the hydrocarbon mixture was introduced through the route of ($e$-$a_3$-$a_1$), and the displacement substance was introduced through the same route as above until the front boundary reached the top of the column A. From the column A, the adsorption band was transferred through the route of ($a_2$-$b_3$-$b_1$) into the column B, and the development was continued by the same flow until the rear boundary of the adsorption band reached the bottom of the column B. When the rear boundary reached the bottom of the column B, the flow of the displacement substance was changed to ($e$-$b_3$-$b_1$), and the route of ($b_2$-$a_5$-$a_1$) from the top of the column B was opened. At the same time, the route of ($a_2$-$a_4$-$f$) was opened, and the displacement substance in the column A was withdrawn by means of nitrogen gas. The development was continued while maintaining the whole flow of ($e$-$b_3$-$b_1$-$b_2$-$a_5$-$a_1$-$a_1$-$a_2$-$a_4$-$f$), until the rear boundary reached the bottom of the column A. Subsequently, the route of introduction of the displacement substance was changed to ($e$-$a_3$-$a_1$), and the route of ($b_4$-$b_2$-$f$) was opened to withdraw the displacement substance in the column B.

When the front boundary reached the top of the column A, the desired composition obtained at the first time from the front boundary was recovered in 35 fractions of each 0.3 ml. The result of analysis showed that the total of o-xylene and m-xylene among the isomers having 8 carbon atoms was 99% or more in the total combined fractions and the displacement substance was detected in the fraction Nos. 1 to 11 but not in the fraction Nos. 12 to 35.

It was confirmed that after recovery of the front boundary composition, the before-half of the adsorption band introduced through the route of ($a_2$-$b_5$-$b_1$) into the column B had formed a fresh front boundary, and development had been initiated. The introduction of starting material was carried out through ($e$-$b_3$-$b_1$), and then the latter-half of the adsorption band was developed through the route of ($a_2$-$b_5$-$b_1$) into the column B. When the rear boundary reached the top of the column A, the rear desired composition liquid was recovered through the route of ($a_2$-$a_4$-$f$). At the same time, the displacement agent was introduced through the route of ($e$-$b_3$-$b_1$) into the column B. In such manner as mentioned above, the starting material was introduced into the central portion of the adsorption band, while displacing the adsorption band from the column A to the column B and from the column B to the column A, and while recovering the desired compositions from the front and rear boundaries. After the adsorption band travelled 16 to 18 m after initiation of the development, the development reached a steady state. The composition was recovered from the front boundary in 35 fractions of each 0.3 ml. As the result of analysis, the displacement substance was detected in the fraction Nos. 1 to 10, but not in the fraction Nos. 11 to 35.

By practice of the above embodiment of the process according to the present invention, it has become possible to perform development repeatedly without desorption of rear or front substance, while maintaining such state that substances other than the hydrocarbon mixture are not substantially migrated into the adsorption band of the substances to be separated in the development column, and thus a separation operation high in separation efficiency and in utilization efficiency can be effected.

Furthermore, as apparently seen from comparison between Examples 21 and 22 or between Examples 23 and 24, migration of displacement substances into the adsorption band can be significantly decreased by use of a specific class of halogenated hydrocarbons.

The following Examples will illustrate further modification of the process of the invention. In these embodiments, during the steady state operation, front substance is present only in the interstices among the adsorbents.

EXAMPLE 26

There were used two jacketed cylindrical development columns of 10 mm. in diameter and 1,000 mm. in length, each of which had tapered inlets and filters at the top and bottom of the column. The development columns and their piping were as shown in FIG. 2 (a). As the adsorbent was used a Y-type synthetic zeolite having an average pore diameter of 9 Å, 73% of which had been substituted by lithium. The zeolite was a granular material having an average volume particle diameter of 0.53 mm., and was used after drying and activation. As the starting material was used a mixture comprising 20% of ethylbenzene, 20% of o-xylene, 40% of m-xylene and 20% of p-xylene, as the front substance (FS) was used nitrogen gas, and as the rear substance (RS) was used dichloromethane. The selectivities of o-xylene, m-xylene and p-xylene to ethylbenzene at a development temperature of 40° C. and a development pressure of 1.5 kg/cm$^2$ was 4.3, 4.8 and 1.03, respectively.

The average plug flow rate in the column was controlled to 1 m/hr in terms of linear velocity, and the operation was initiated according to FIG. 2 (a). At the time of initiation of the operation, both the columns A and B packed with the adsorbents were filled with nitrogen gas, and adjusted to the development conditions. Subsequently, the hydrocarbon mixture was fed in a plug flow through the route of (e-a$_3$-a$_1$) to form a front boundary in the column A. The feeding was continued until the front boundary reached the top of the column A, whereupon RS was introduced through the same route as above. From the column A, the adsorption band was transferred through the route of (a$_2$-b$_5$-b$_1$). When the flow of RS reached b$_1$, the route of introduction of RS was changed to (e-b$_3$-b$_1$), and the route of (b$_1$-b$_2$-b$_4$) from the top of the column B was opened. At the same time, FS was introduced through the route of (f-a$_4$-a$_2$) into the column A to displace RS present in the interstices in the column A by FS. When the front boundary in the column B reached the top, the route of (b$_2$-a$_5$-a$_1$) was opened. Thereafter, the development was continued, while maintaining the whole flow of (e-b$_3$-b$_1$-b$_2$-a$_5$-a$_1$-a$_2$-a$_4$-f), until the front boundary reached the top of the column A, and the desired composition in the vicinity of the front boundary was recovered. During this time, the route of introduction of RS was changed to the route of (e-a$_3$-a$_1$) when RS reached a$_1$, and FS was introduced through the route of (f-b$_4$-b$_2$) to displace RS present in the interstices in the column B therewith.

The desired composition at the first time from the front boundary was recovered in 20 fractions of each 0.285 ml. As the result, the total of ethylbenzene and p-xylene among the isomers having 8 carbon atoms in the combined fractions was found to be 99% or more. RS was detected in the fraction Nos. 1 to 7 but was not detected in the fraction Nos. 8 to 20. It was observed that the front boundary, which had been introduced through the route of (a$_2$-b$_5$-b$_1$) into the column B, had formed a fresh, favorable boundary. The development was conducted while introducing the starting material through (e-b$_3$-b$_1$) and recovering the desired composition through (a$_2$-a$_4$-f). When the front boundary reached the top of the column B, the desired composition was recovered through (b$_2$-b$_4$-f) in 20 fractions of each 0.29 ml. As the result of analysis, it was found that the concentration of ethylbenzene and p-xylene based on the total amount of the hydrocarbon mixture was 99% or more, and no RS was entrained therein before the fraction No. 10. In this manner, the desired compositions were recovered from the front and rear boundaries each ten times from the columns A and B. As the result, the composition recovered in every time was constant.

EXAMPLE 27

There were prepared three jacketed cylindrical development columns of 30 mm. in diameter and 100 cm. in length, each of which had filters and distribution means as inlets at the top and bottom of the column. These columns were assembled in such a manner as shown in FIG. 2 (b). As the adsorbent was used a sodium type ion having an average pore diameter of 8 Å which was a crystal of the Faujasite type. As the hydrocarbon mixture was used a distillate obtained by fractionating a mixture of reformates from petroleum naphtha which contained hydrocarbons with 6 to 8 carbon atoms as principal components, and then recovering fractions distilled at 95° to 124° C. The composition of the distillate was 48% of toluene and 52% of a non-aromatic mixture. At the time of initiation of development, all the columns A, B and C were filled with nitrogen gas, and as RS was used n-butyl ethyl ether. At the time of initiation, the boundary with FS was formed, and, at the stages after steady state, the desired composition from the front boundary was recovered at the column top. After the steady state, FS was flowed down through the development column filled with RS to fill the interstices with FS. In this case, 82% of total RS in the column was in the interstices, and it was confirmed that the said interstices had been replaced by FS. The desired compositions obtained after the steady state were such that a liquid comprising 22% of a hydrocarbon mixture enriched with non-aromatics and 78% of RS, which hydrocarbon mixture was composed of 99.1% of non-aromatic compounds and 0.9% of toluene, was recovered from the front boundary, while a liquid comprising 31% of a toluene-rich hydrocarbon mixture and 69% of RS, which hydrocarbon mixture was composed of 99.2% of toluene, was recovered from the rear boundary.

When FS is introduced into the columns filled with RS to replace RS in the interstices in the columns, the replaced phase can be simulated to the phase wherein the entire space is preoccupied by FS, and, when the development is performed repeatedly, a relatively stable front boundary can be formed.

The following examples illustrate the embodiments wherein the present process is combined with isomerization process.

EXAMPLE 28

As the starting mixture was used as C$_8$ isomer mixture comprising (by weight) 20% of ethylbenzene, 20% of p-xylene, 40% of m-xylene and 20% of o-xylene. As the adsorbent in the separation development column was used a crystalline aluminosilicate having a pore diameter of 9 Å and a structure of (Ca, Mn).O.SiO$_2$.2.5Al$_2$O$_3$.wH$_2$O (where the ratio of Ca to Mn is 72% to 28%, and w is 9.0), as the front substance was used nitrogen gas, as the rear substance was used methylene chloride, and as the isomerization catalyst was used a silica-alumina system catalyst. In addition, steam was introduced in slight excess of the starting material. The operations were performed according to the flow shown in FIG. 7.

The separation development column c was 10 mm. in diameter and 1,000 mm. in length, and the isomerization reaction column f was 40 mm. in diameter and 300 mm. in length. The column c was adjusted to 40° C. and 1.8 atm., while the column f to 530° C. and 1.5 atm. The starting mixture was introduced at a rate of 3.6 ml/hr, low boiling components were removed in the light-cut distillation column a, high boiling components were removed in the heavy-cut distillation column b, and 3.5 ml/hr of the pre-treated flow was introduced into the column c. The operation was conducted continuously to separate 1.8 ml/hr of production flow, and 3.5 ml/hr of isomerization flow III was taken out. This isomerization flow was introduced into the column d to remove the rear substance, and 2.7 ml/hr of flow XI was introduced through the preheater e into the isomerization reaction column f. Subsequently, 1.7 ml/hr of isomerized flow was taken out and combined with IV and I, and the same operation as above was again repeated. After a complete equilibrium had been reached by repeating the operation, the rate and composition of each flow at equilibrium were measured and analyzed to obtain such results as shown below.

Table 2

| Flow No. | I | II | III | IV |
|---|---|---|---|---|
| Flow rate (ml/hr) | 1.94 | 1.80 | 3.92 | 3.93 |
| Ethylbenzene (%) | 20.0 | 24.6 | 0.40 | 1.80 |
| p-Xylene (%) | 20.0 | 74.9 | 1.10 | 24.30 |
| m-Xylene (%) | 40.0 | 0.40 | 67.40 | 48.50 |
| o-Xylene (%) | 20.0 | 0.10 | 31.25 | 22.0 |
| Low boiling component (%) | 0 | 0 | 0 | 3.0 |
| High boiling component (%) | 0 | 0 | 0 | 0.4 |

From Table 2, the recovery ratio was 92.8%.

EXAMPLE 29

Separation was performed by using as the starting flow the same mixture as in Example 28. The flow sheet was as shown in FIG. 8. The operation in the separation column was effected in entirely the same manner as in Example 28, and the rate of production flow II was controlled to 1.80 ml/hr like in Example 27 to obtain such results as shown in Table 3.

Table 3

| Flow No. | I | II | III |
|---|---|---|---|
| Flow rate (ml/hr) | 4.60 | 1.80 | 2.80 |
| Ethylbenzene (%) | 20.0 | 51.8 | 0.44 |
| p-Xylene (%) | 20.0 | 47.7 | 2.19 |
| m-Xylene (%) | 40.0 | 0.4 | 65.5 |
| o-Xylene (%) | 20.0 | 0.1 | 31.9 |
| Low boiling component (%) | 0 | 0 | 0 |
| High boiling component (%) | 0 | 0 | 0 |

From Table 3, the recovery ratio was 39.1%.

EXAMPLE 30

Using a $C_8$ isomer mixture comprising (by weight) 20% of ethylbenzene, 20% of p-xylene, 40% of m-xylene and 20% of o-xylene, development was performed according to such flow as shown in FIG. 9, which was based in principle on the flow shown in FIG. 5. As the adsorbent in the first separation development column c was used entirely the same adsorbent as in Example 28, and as the adsorbent in the second separation development column g was used a crystalline aluminosilicate having a pore diameter of 9 Å and a structure of $(Ba).O.SiO_2.2.5Al_2O_3.wH_2O$ (where Ba is a substituted metal, and w is 9.0). The operational conditions in the columns a, b, c, d, e and f were entirely the same as in Example 28. In the second separation column g, butane was used as the front substance, and methyl chloride as the rear substance. The production flow II had a flow rate of 1.74 ml/hr and was composed of 24.7% of ethylbenzene, 74.8% of p-xylene, and 0.50% of the total of m-xylene and o-xylene. The column g was 5 mm. in diameter and 800 mm. in length, and the development was effected at 25° C. and 25 atm. The product XIII separated from the column g, which contained 99.8% of ethylbenzene, was recovered at a flow rate of 0.38 ml/hr from the front boundary, and a separated substance containing 99.52% (based on $C_8$) of p-xylene was obtained at a flow rate of 1.36 ml/hr in a mixing ratio of 1:1 to the rear substance. In the column h, the rear substance was removed to obtain a production flow as the flow XVI. In the above manner, such mass balances as set forth in Table 4 were obtained.

Table 4

| Flow No. | I | XIII | XVI |
|---|---|---|---|
| Flow rate (ml/hr) | 1.94 | 0.38 | 1.36 |
| Ethylbenzene (%) | 20.0 | 99.8 | 0.2 |
| p-Xylene (%) | 20.0 | 0.1 | 99.5 |
| m-Xylene (%) | 40.0 | 0.1 | 0.2 |
| o-Xylene (%) | 20.0 | 0.1 | 0.1 |

From Table 4, the recovery ratio of ethylbenzene was 97.7%, and that of p-xylene was 34.9%.

EXAMPLE 31

As the raw material was used a $C_8$ isomer mixture comprising 25% of p-xylene, 50% of m-xylene and 25% of o-xylene, and as the adsorbent in the separation development column was used an L-type zeolite, 33.5% of which had been substituted by Ba. As the front substance was used methane, as the rear substance was used fluorobenzene, and as the isomerization catalyst was used an alumina-rich silica-alumina catalyst. The operations were performed according to the flow shown in FIG. 7. The separation development column c was 10 mm. in diameter and 500 mm. in length, and the isomerization reaction column f was 30 mm. in diameter and 300 mm. in length. The column c was adjusted to 120° C. and 5.2 atm., while the column f to 420° C. and 1.1 atm. The raw material was introduced at a flow rate of 4.3 ml/hr, low boiling components and high boiling components were removed in the columns a and b, respectively, 4.2 ml/hr of flow was introduced into the column c, and 1.9 ml/hr of production flow and 6.2 ml/hr of isomerization flow III were taken out. This isomerization flow was introduced into the column d to remove the rear substance, and 4.1 ml/hr of flow XI was introduced through the preheater e into the column f. Subsequently, the isomerized flow was taken out and combined with I, and the same operation as above was repeated to reach an equilibrium. Flow amounts and purities after the equilibrium were as shown in Table 5.

Table 5

| Flow No. | I | II | III | IV |
|---|---|---|---|---|
| Flow amount (ml/hr) | 2.52 | 2.30 | 7.59 | 7.59 |
| p-Xylene (%) | 25 | 99.8 | 1.1 | 21.8 |
| m-Xylene (%) | 50 | 0.2 | 65.9 | 50.2 |
| o-Xylene (%) | 25 | 0.1 | 33.0 | 23.1 |
| Low boiling component (%) | 0 | 0 | 0 | 4.1 |
| High boiling component (%) | 0 | 0 | 0 | 0.8 |

From Table 5, the per-pass yield of p-xylene was 36.4%, and the total yield of p-xylene based on $C_8$ isomer was 91.1%.

What we claim is:

1. A process for continuously separating original liquid hydrocarbon mixtures containing at least two hydrocarbon components each having a critical temperature of at least 70° C. and a melting point no higher than 320° C. which comprises:
   (a) feeding said mixture in plug flow to a column packed with adsorbents having a selectivity for one component compared to other components of at least 1.2 to form an adsorption zone in which the components are distributed between the adsorbents and the liquid in the void volume, (b) feeding, in plug flow, a rear substance which selectively desorbs components which are adsorbed on the adsorbents, and continuing to feed said rear substance at a rate so as to move the hydrocarbon mixture forward while maintaining a boundary between the rear fraction of the hydrocarbon mixture and the forward edge of the rear substance to distribute the hydrocarbon components in an adsorption zone so that the front edge of the hydrocarbon mixture is enriched in the least readily adsorbed hydrocarbon component and the boundary formed at the rear edge of the hydrocarbon mixture and the forward edge of the rear substance is enriched in the most strongly adsorbed hydrocarbon component, thereby creating gradient concentrations in the moving hydrocarbon mixture increasing towards the trailing edge thereof in the case of the most strongly adsorbed hydrocarbon component, and decreasing towards the said trailing edge in the case of the least strongly adsorbed hydrocarbon component, thereby forming a first fraction at the front edge segment enriched in the least strongly adsorbed component and a second fraction at the rear edge segment enriched in the most strongly adsorbed component, (c) recovering at least one of said fractions, (d) feeding an additional portion of said hydrocarbon mixture to said column and repeating Steps (b) and (c); said column while in continuous operation containing a plurality of said hydrocarbon mixtures separated by a desorbent liquid segment.

2. A process as in claim 1 wherein the portion of the hydrocarbon mixture remaining after recovery is enriched by the addition of more original hydrocarbon mixture, returned to the said column behind the said rear substance and additional rear substance is fed to the column behind the said hydrocarbon mixture to thereby move the returned hydrocarbon mixture through the column and increase the concentration of the least strongly adsorbed substance at the front boundary of the hydrocarbon mixture and concurrently increase the concentration of the most strongly adsorbed substance at the rear boundary to form new first and second fractions; and, thereafter, recovering at least one of second fractions.

3. A process as in claim 1 wherein the additional hydrocarbon mixture of Step (d) is fresh hydrocarbon mixture.

4. A process as in claim 1 employing a plurality of columns comprising a separation unit in which the portion of the hydrocarbon mixture remaining after recovery of at least one of said fractions from the first column is supplemented with original hydrocarbon mixture and Steps (a) and (b) are repeated in successive columns until new first and second fractions of predetermined compositions are produced in a selected column, and at least one of said fractions is recovered, the step of adding supplemental original hydrocarbon mixture beng repeated after each recovery step and before addition to a succeeding column.

5. A process as in claim 4 wherein one of said first and second recovered fractions is enriched in a desired isomer and the other of said fractions is depleted is a desired isomer, and the fraction depleted in the desired isomer is subjected to an isomerization process to convert the undesired isomer to the desired isomer and produce a fraction rich in the desired isomer.

6. A process as in claim 4 wherein the produced fraction rich in the desired isomer due to the isomerization process is returned to a column for further purification.

* * * * *